United States Patent [19]

Burke et al.

[11] 3,994,950

[45] Nov. 30, 1976

[54] XANTHATE-LEWIS ACID COMPLEXES

[75] Inventors: Noel I. Burke, Danville; Douglas J. Bridgeford, Champaign; Albin F. Turbak, Danville, all of Ill.

[73] Assignee: Tee-Pak, Inc., Chicago, Ill.

[22] Filed: Dec. 8, 1975

[21] Appl. No.: 638,713

Related U.S. Application Data

[60] Continuation of Ser. No. 205,415, Dec. 6, 1971, abandoned, which is a division of Ser. No. 856,821, Sept. 10, 1969, Pat. No. 3,666,738.

[52] U.S. Cl. ............................................ 260/455 B
[51] Int. Cl.² ....................................... C07C 154/02
[58] Field of Search ..................... 260/455 B, 455 R

[56] References Cited
UNITED STATES PATENTS 3,666,739    9/1969    Burke et al. ................. 260/455 R

FOREIGN PATENTS OR APPLICATIONS 999,436    10/1949    France ............................. 260/455
43-13,968    9/1950    Japan ............................ 260/455 B

*Primary Examiner*—Lewis Gotts
*Assistant Examiner*—D. R. Phillips
*Attorney, Agent, or Firm*—Paul Shapiro; Joseph E. Kerwin; William A. Dittmann

[57] ABSTRACT

Xanthate esters of the form:

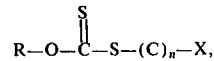

where R is an alkyl function having at least one H in a position alpha to the R—O bond, $(C)_n$ is a linear alkyl function either substituted or unsubstituted, with $n = 1 - 3$, X has a basicity greater than the $>C=S$ function and comprises a C or S containing functional group having at least one double or triple bond to a hetero atom, the functional group being connected to $(C)_n$ through C or S; are reacted with Lewis acids, either neat or in non-protonic non-aqueous solvents, to yield novel Lewis acid complexes of the esters. The Lewis acid — xanthate ester complex is decomposed by admixture with water or a protonic non-aqueous solvent, e.g. methanol, ethanol, etc., glycol, cellosolve, liquid ammonia, lower alkyl primary or secondary amines, aniline, etc., to yield an unsaturated derivative of R.

3 Claims, No Drawings

XANTHATE-LEWIS ACID COMPLEXES

CROSS-REFERENCE TO RELATED APPLICATION

This application is a continuation of copending application Ser. No. 205,415 filed Dec. 6, 1971, now abandoned, which is a division of application Ser. No. 856,821 filed Sept. 10, 1969 and now issued as U.S. Pat. No. 3,666,738.

BACKGROUND OF THE INVENTION

1. Field of the Invention

This invention relates to novel Lewis acid — xanthate ester complexes and to method to prepare the same. These complexes are useful in the preparation of unsaturated derivatives or decomposition products by hydrolysis.

DESCRIPTION OF THE PRIOR ART

The production of unsaturated compounds from alcohols has been known for a long time. However, most of the methods of dehydration involve the treatment of the alcohol with a strong acid or the thermal decomposition of the alcohol or one of its derivatives. Some of the better known and most often used methods of dehydration are the use of an acid such as sulfuric acid, phosphorus pentoxide, phosphorus oxychloride, and other strong acids; the pyrolysis of the alcohol on alumina, the pyrolysis of an ester of the alcohol, usually the acetate or benzoate, and the pyrolysis of a xanthate ester of the alcohol. Not all compounds will survive the treatment of a strong acid and/or pyrolysis. Polymeric alcohols as a class will usually decompose to a black, often tarry mass if a strong acid or thermal decomposition technique is used in an attempt to produce an unsaturated compound from the alcohol.

The Chugaev reaction prepares certain unsaturated compounds by pyrolysis of alkyl xanthate esters. This reaction is run anhydrous at a high temperature and is applicable only to the production of a limited number of unsaturated compounds.

Recently, Rogovin has produced an unsaturated cellulose by making the tosylate, displacing the tosylate with iodide, and finally dehydrohalogenating the iodide derivative. Unlike previous attempts to dehydrate cellulose by pyrolitic means, the Rogovin procedure gave a white unsaturated cellulose with a double bond in the $C_5 - C_6$ position. While the Rogovin procedure gives a pure product, the cost of the reagents involved makes the economic practicality of the procedure quite doubtful.

SUMMARY OF THE INVENTION

This invention was based upon the discovery that simple and complex, monomeric and polymeric, unsaturated compounds may be prepared by hydrolysis of certain Lewis acid - xanthate ester intermediates.

Complexes of Lewis acids with xanthate ester of the form:

where R is an alkyl function having at least one H in a position alpha to the R—O bond, $(C)_n$ is a linear alkyl function either substituted or unsubstituted, with $n = 1 - 3$, X has a basicity greater than the $>C=S$ function and comprises a C or S containing functional group having at least one double or triple bond to a hetero atom, the functional group being connected to $(C)_n$ through C or S, and A is a Lewis acid; will decompose upon admixture with water or a protonic non-aqueous solvent, e.g. methanol, ethanol, etc., glycol, cellosolve, liquid ammonia, lower alkyl primary and secondary amines, aniline, etc., to yield an unsaturated derivative of R. The term "alkyl function" as used above refers to a functional group which is alkyl in structure which may be complete in itself or may be substituted. The alkyl function R may be a simple or complex, substituted or unsubstituted, monomeric or polymeric, function but must have at least one H is a position alpha to the R - O bond. $(C)_n$ is an alkyl function of the form, $—CR_2^1—$, $—CR_2^1CR_2^2—$, or $—CR_2^1CR_2^2CR_2^3—$ where $R^1$, $R^2$, and $R^3$ may be hydrogen or inert substituents.

This invention arose as a result of work done on certain cellulose xanthate derivatives and an effort to establish a mechanism for the decomposition of xanthates. The work which we carried out appears to support the mechanism which we have proposed and which is described herein for a better understanding of the invention. The proposed mechanism however merely represents our best current theory of the mechanism of the reaction and should not be considered to be a completely accurate description of the way that the reaction takes place.

During the course of some work on cellulose xanthate derivatives, we attempted to determine the reason that cellulose xanthate S-propane sulfonate, which is water soluble, would not wash off fabrics that had a 2 – 4% addon of the polymer. This investigation showed that at least part of the sulfur in the derivative was being lost upon heating, both on the fabric and in solution. Since cellulose xanthate derivatives are extremely complex we decided that at least the early part of the investigation should be done on simple model compounds.

The isopropyl xanthate S-propane sulfonate derivatives was prepared, then dissolved in water at pH 4.5 and the solution heated at 100° C. The gases evolved were examined using gas chromatography. The gases that were expected from hydrolysis, viz. carbon disulfide, carbonyl sulfide, carbon dioxide, hydrogen sulfide, and in some cases sulfur dioxide, were found as well as an unidentified gas. Due to the long retention time of this gas it was thought to be an organic material. A sample of the gas was collected and identified by infrared spectroscopy as propylene. The presence of propylene in the evolved gases was totally unexpected in view of previous conceptions of the mechanism of the xanthate decomposition.

In order to be sure of the presence and the approximate amount of propylene, the decomposition was repeated, but the evolved gases were separated and the hydrocarbon passed into bromine in carbon tetrachloride. The excess bromine was back titrated and the organic portion was removed and the carbon tetrachloride evaporated to leave an oil. The infrared spectrum of this material was identical with the infrared spectra of an authentic sample of dibromopropane. It was thought at first that the reaction might be similar to the well known Chugaev reaction which utilizes alkyl esters of xanthates in pyrolysis. However, the Chugaev reaction is run anhydrous at a high temperature. Nevertheless, S-methyl-2-propyl xanthate was prepared and decomposed in aqueous media at pH 4.5 . This yielded only minute amounts of propylene.

Since the decomposition did not seem to be a modification of the Chugaev reaction and since there is no precedent for this reaction in the literature, a variety of xanthate derivatives were prepared in an attempt to determine the utility and scope of the reaction.

The electron withdrawing power of the attached group was considered necessary for the decomposition reaction. Therefore, the carboxy methyl group was prepared and decomposed over a range of pH. The pH range of 4–5 seems to give the best result. At pH 4.5 the reaction is relatively slow for many derivatives but gave good yields if carried out for a long enough time.

In the investigation, various derivatives were prepared of xanthates of n-propanol, 2-propanol, 2-butanol, cyclohexanol and cholesterol. The derivatives used included esters of the alcohol xanthates prepared from derivatives of 2-propanone, acetaldehyde dialkyl acetal, cyanoethyl and cyanolmethyl. The decomposition of each of these derivatives seems to be a critical function of the pH of the media if a reasonable yield is to be obtained. It seemed possible that the pH dependence of the reaction was due to competing reactions. The primarily competing reaction that would reduce the yield is hydrolysis. At low pH, the hydrolysis of xanthate esters is acid-catalyzed and at high pH the hydrolysis is base catalyzed. If the rate dependent step of the decomposition to produce an unsaturated compound is a steric one, that is, the molecule must be in a particular configuration, then the pH dependence is one of reduction of by-products and does not directly affect the rate of decomposition. Since the time of these reactions is generally quite long, it is reasonable that hydrolysis must be repressed if the decomposition to an unsaturated product is to take place.

With the pH dependence in mind and the apparent necessity for the presence of an electron withdrawing group, the following mechanism is proposed:

the electron withdrawing power of the attached group, but the ability of the group to produce a carbonium ion on the carbon atom containing the group. Thus, a nitroethane ester would not be expected to give any unsaturated product. When the nitroethane derivative of isopropyl xanthate was treated for 150 hours no propylene was obtained.

The proposed mechanism also indicates that any atom in the intermediate that is able to support a positive charge would probably not undergo the decomposition. The types of derivatives that the mechanism predicts that would not undergo the decomposition are the dithiocarbamates and amide derivatives among others.

When dithiocarbamate esters were treated they all failed to give the corresponding unsaturated compounds. Likewise, amide derivatives of xanthates failed to undergo the decomposition, as predicted.

In the case of the amides, the protonated carbonyl would be the most stable form of the ion and in the case of dithiocarbamates the charge would be relatively stable on the nitrogen; however, this intermediate could easily add water to give the amine that was used to prepare the dithiocarbamate.

The proposed mechanism would indicate that any molecule that can obtain the required steric configuration and conforms to the formula given above (in the abstract of the disclosure) will yield the corresponding unsaturated compound on decomposition. The sulfonate group does not fit the same mechanism as the other formulae; however, this group was the only one that gave sulfur dioxide in the gas chromatographic analysis of evolved gases. A mechanism for decomposition of the sulfonate derivative involves the formation of a 6 membered hetero cycle containing sulfur, as an intermediate, with an accompanying splitting off of sulfurous acid, which decomposes to yield sulfur dioxide. The hetero cyclic intermediate decomposes to yield the desired unsaturated compound.

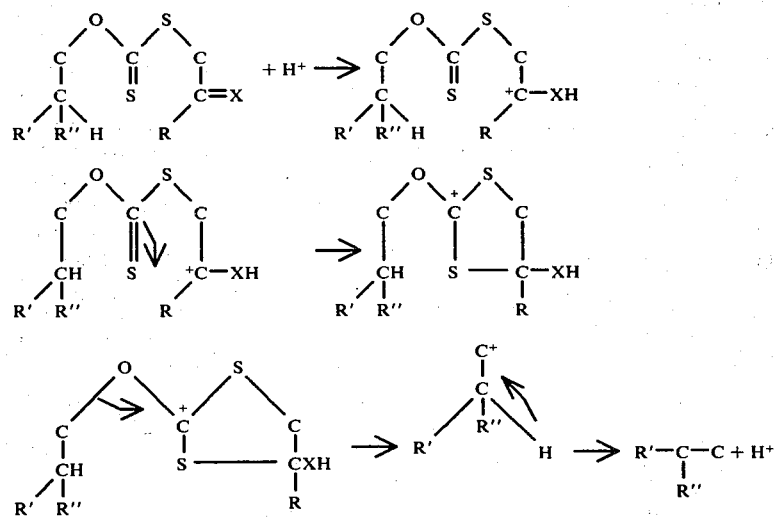

In the above mechanism, the compound is shown in skeletal form. The unsatisfied valences on the carbon atoms are considered to be connected to hydrogen radicals, or any inert substituent or functional group.

The postulated mechanism would also be applicable to the formation of a 6 membered ring as the transitory "intermediate." This mechanism indicates that it is not The proposed mechanism (and experiments which we have done) indicates that the decomposition of the xanthate esters can be carried out more effectively by formation of a complex of a Lewis acid with the xanthate ester followed by hydrolysis of the Lewis acid - xanthate ester intermediate in water or in a protonic non-aqueous solvent. In carrying out this process, a complex is formed of the xanthate ester with any Lewis acid that will attach to the derivative group and not the thione sulfur of the xanthate group. The xanthate ester - Lewis acid complex may be formed neat or in solution or dispersion in a non-protonic non-aqueous solvent. Any of the Lewis acids, e.g. $BF_3$, $SnCl_2$, $ZnCl_2$, $FeCl_3$, $SnCl_4$, $AlCl_3$, etc. may be used in forming the complex with the xanthate esters, with the understanding that the Lewis acid selected must be of an acid strength such that it will form a salt or complex preferentially with the derivative functional group rather than the thione sulfur of the xanthate group. Also, when the preparation of the Lewis acid complex is carried out in solution or dispersion in a non-aqueous solvent, a Lewis acid must be used which does not form a stronger complex with the solvent than with the derivative group in the xanthate ester. Any suitable solvent may be used, including ethers such as diethyl ether or dioxane, ketones, such as acetone or methylethyl ketone, esters, chlorinated hydrocarbons, hydrocarbon fractions, such as pentane, benzene, petroleum ether or other petroleum distillates, carbon disulfide, etc. While all of the Lewis acids and all non-aqueous solvents which are inert toward the xanthate esters may be used in the preparation of the Lewis acid - xanthate ester derivatives, it is understood that the solvents and the Lewis acids must be selected so that they are compatible with each other and with the xanthate ester used. Thus, the solvent used must always be inert toward the xanthate ester and must not form a complex with the Lewis acid which is stronger than the complex or salt formed with the xanthate ester. Also, the Lewis acid selected must be of an acid strength such that it will combine preferentially with the ester functional group (also referred to as the derivative functional group) rather than the thione sulfur in the xanthate group. The Lewis acid is used in an amount just sufficient to form the desired complex with the ester or derivative functionality so that no excess is present to complex with the xanthate group. As an example $BF_3$ is a very strong Lewis acid and is effective only with esters that include highly basic functions such as the nitrile group. Where the esters are less basic it is necessary to use weaker Lewis acids such as $SnCl_4$, $ZnCl_2$, $FeCl_3$, etc.

DESCRIPTION OF THE PREFERRED EMBODIMENTS

In the following examples there are illustrated a variety of starting materials and reaction conditions which illustrate the general operability of our invention as described broadly above. The examples illustrate the general preparation of olefins by hydrolysis of certain Lewis acid - xanthate ester intermediates in aqueous media or non-aqueous active hydrogen containing solvents.

EXAMPLE 1

Sodium cyclohexyl xanthate and acrylonitrile were reacted in solution in cyclohexanol to produce the S-cyanoethyl ester of cyclohexyl xanthate. The solution was diluted with a large excess of water and extracted with diethyl ether. The ether was removed from the extract under vacuum and S-cyanoethylcyclohexyl xanthate recovered as the product in substantially quantitative yield based on the sodium cyclohexyl xanthate charged.

This S-cyanoethylcyclohexyl xanthate was dissolved in diethyl ether at 5% concentration and treated with approximately stoichiometric amounts of $BF_3$ to produce a complex of the $BF_3$ on the nitrile portion of the ester.

The $BF_3$ - xanthate ester complex was mixed with an excess of water and hydrolyzed almost immediately. After about 10 minutes, there was obtained and separated cyclohexene in a yield of 75% based on the xanthate ester charged.

When this procedure is repeated and the $BF_3$ complex mixed with other active hydrogen containing materials, including methanol, ethanol, glycerin, glycol, liquid ammonia, methylamine, dimethyl amine, aniline, etc. the complex is decomposed (in a manner corresponding approximately to the hydrolysis reaction) yielding cyclohexene in high yield.

EXAMPLE 2

The procedure of Example 1 was repeated except that the S-cyanoethylcyclohexyl xanthate was complexed with $BF_3$ by reaction in pentane. The hydrolysis was carried out in water with a yield of 68% after 10 minutes.

EXAMPLE 3

S-ethylcarboxymethyl ester of cyclohexyl xanthate was prepared by reaction of ethyl chloracetate with sodium cyclohexyl xanthate in water. The xanthate ester was recovered by extraction with diethyl ether and the solvent subsequently removed under vacuum.

The S-ethylcarboxymethyl ester of cyclohexyl xanthate was dissolved in pentane at a 10% concentration and treated with $BF_3$ in essentially stoichiometric quantities for 24 hours to produce a $BF_3$ - xanthate ester complex. The complex was mixed with water where it decomposed in a few minutes to give a 20% yield of cyclohexene.

This example illustrates the loss of yield which occurs where the Lewis acid is strong and tends to complex to a substantial degree both with the xanthate group and the ester group.

EXAMPLE 4

S-cyanoethylcyclohexyl xanthate is prepared as described in Example 1 and dissolved in nitrobenzene. An approximately stoichiometric amount of aluminum chloride is added to complex with the nitrile portion of the xanthate ester. A precipitate is formed almost immediately comprising the aluminum chloride complex of the xanthate ester. The precipitate is recovered by filtration and hydrolyzed by addition of water. The hydrolysis reaction is quite rapid and produces cyclohexene in about a 60% yield in a few minutes.

When this procedure is repeated and the aluminum chloride complex mixed with other active hydrogen containing solvents, viz. methanol, ethanol, glycerin, glycol, phenol, ammonia, ethanolamine, methylamine, dimethyl amine, etc. the complex decomposes rapidly to yield cyclohexene.

EXAMPLE 5

Sodium 2-propyl xanthate and sodium chloracetate are reacted in isopropanol to yield S-carboxymethyl-2-propyl xanthate. The xanthate product is recovered by crystallization from solution as a crystalline solid.

This S-carboxymethyl-2-propyl xanthate is slurried in methylethyl ketone and treated with sufficient ferric chloride to form a complex (1:1 mole ratio) which settles from the slurry.

The FeCl$_3$ - xanthate complex is added to an excess of water where it is hydrolyzed rapidly with evolution of propylene. The hydrolysis of the complex yields about 55% propylene in 30 minutes. The decomposition of the ferric chloride-xanthate complex in other active hydrogen containing solvents, such as methanol, ethanol, glycerin, glycol, phenol, ethanolamine, methylamine, dimethyl amine, etc. yields substantial quantities of propylene in a few minutes time.

EXAMPLE 6

Sodium 2-butyl xanthate and ethyl chloracetate are reacted in butanol to yield S-ethylcarboxymethylate-2-butyl xanthate. The solution is diluted with a large excess of water and extracted with diethyl ether. The ether is removed from the extract under vacuum to leave a residue of the S-ethylcarboxymethylate-2-butyl xanthate in substantially quantitative yield.

This S-ethylcarboxymethylate-2-butyl xanthate is dissolved in perchlorethylene and treated with sufficient stannic chloride to precipitate a 1:1 molar complex. The stannic chloride-xanthate ester complex is recovered by filtration (or by centrifuging) and hydrolyzed by addition of an excess of water. The hydrolysis reaction is quite rapid and evolves up to 70% yield of butylene with 30 to 60 minutes.

When this procedure is repeated and the stannic chloride - xanthate ester complex is decomposed by treatment with other active hydrogen containing materials, such as methanol, ethanol, glycerin, glycol, phenol, ethanolamine, methylamine, dimethyl amine, etc., butylene is evolved rapidly in high yield.

EXAMPLE 7

Sodium 1-octyl xanthate and chloracetone are reacted in equimolar portions in ethanol to yield S-(2-propanone)1-octyl xanthate. The solution is diluted with a large excess of water and extracted with diethyl ether. The ether is removed from the extract leaving the xanthate ester in essentially quantitative yield.

The S-(2-propanone)-octyl xanthate is dissolved in 5% concentration in dioxane and sufficient zinc chloride added to precipitate the zinc chloride - xanthate ester complex.

The zinc chloride - xanthate ester complex is separated by filtration (or by centrifuging) and treated with an excess of water to decompose the complex. The hydrolysis of the complex is rapid and produces 1-octene in yields of up to 70% – 80% in 1 hour. The zinc chloride - xanthate ester complex can similarly be decomposed by reaction with other active hydrogen containing solvents as described in the previous examples.

EXAMPLe 8

1,4-butylene glycol dixanthate disodium salt and chloracetonitrile (in a 1:2 mole ratio) are reacted in solution in ethanol to yield the di-cyanomethyl ester of the butylene glycol dixanthate. The solution is diluted with a large excess of water and extracted with diethyl ether. The ether is removed from the extract under vacuum and a substantially quantitative yield of the dixanthate diester is obtained.

This butylene glycol dixanthate di-cyanomethyl ester is dissolved in ethyl acetate at about a 5% concentration and boron trichloride is added in an amount equivalent to the nitrile functionality. A boron trichloride — xanthate ester complex is precipitated from the solution and recovered by filtration.

The boron trichloride — xanthate ester complex is mixed with an excess of water, maintained at pH 7 – 8, and hydrolyzed rapidly. In less than 1 hour there is obtained a 60 – 70% yield of butadiene. The boron trichloride — xanthate diester complex similarly is decomposed upon admixture with other active hydrogen containing solvents, as described in the other examples, to yield butadiene rapidly in high yield.

EXAMPLE 9

Sodium cyclohexyl xanthate and ethyl chloracetate are reacted in solution in cyclohexanol to yield S-ethylcarboxymethylate cyclohexyl xanthate. The solution is diluted with a large excess of water and extracted with diethyl ether to recover the xanthate ester. The ether is removed under vacuum to recover the xanthate ester in substantially quantitative yield.

This S-ethylcarboxymethylate cyclohexyl xanthate is dissolved in dimethylformamide in a concentration of about 10%. To this solution there is added antimony trichloride in an amount just sufficient to complex with the xanthate ester. The antimony trichloride — xanthate ester complex which forms precipitates almost immediately from the solution and is recovered by filtration.

The antimony trichloride — xanthate ester complex is diluted with an excess of water and hydrolyzes almost to completion in 1 hour. There is a yield of about 30 – 40% cyclohexene. The antimony trichloride — xanthate ester complex similarly decomposes rapidly in other active hydrogen containing solvents (as in the other examples) to yield cyclohexene in fair yield.

PREPARATION OF UNSATURATED DERIVATIVES OF POLYMERIC ALCOHOLS

The following examples illustrate the application of this process to the preparation of unsaturated derivatives of polymeric alcohols by hydrolysis (or decomposition in other active hydrogen containing solvents) of Lewis acid complexes of polymeric alcohol xanthate esters.

EXAMPLE 10

Sodium cellulose xanthate is reacted in aqueous suspension (or solution) with chloracetonitrile to yield the cyanomethyl ester. After filtering and drying, the xanthate ester is then slurried in diethyl ether at a concentration of about 5% and treated with a stoichiometric amount (with respect to the nitrile) of boron trifluoride diethyl etherate. The boron trifluoride — xanthate ester complex is produced in high yield.

Next, the boron trifluoride — xanthate ester complex is treated with an excess of water to hydrolyze the complex. The reaction goes to completion in a few minutes and gives a yield to about 40 – 50% of unsaturated cellulose, having unsaturation present both as vinyl unsaturation, i.e. in the 6 position, and as ring unsaturation.

When the same procedure is repeated except that the boron trifluoride — xanthate ester complex is decomposed by treatment with other active hydrogen containing solvents (as described in the previous examples) there is obtained a good yield of unsaturated cellulose in a relatively short time.

EXAMPLE 11

Sodium starch xanthate is reacted in aqueous suspension (or solution) with chloracetonitrile to yield the cyanomethyl ester. The xanthate ester is then slurried in pentane at a concentration of about 5% and treated with a stoichiometric amount of boron trifluoride (with respect to the nitrile). The boron trifluoride — xanthate ester complex is produced in high yield.

Next, the boron trifluoride — xanthate ester complex is treated with an excess of water to hydrolyze the complex. The reaction goes to completion in about 1 hour and gives a yield of about 40 – 50% of unsaturated starch, having unsaturation present both as vinyl unsaturation, i.e. in the 6 position, and as ring unsaturation.

When the same procedure is repeated except that the boron trifluoride — xanthate ester complex is decomposed by treatment with other active hydrogen containing solvents (as described in the previous examples) there is obtained a good yield of unsaturated starch in a relatively short time.

EXAMPLE 12

Sodium polyvinyl alcohol xanthate is reacted with chloracetonitrile in aqueous solution to yield the cyanomethyl ester.

This cyanomethyl polyvinyl alcohol xanthate ester is then slurried in methylethyl ketone at 10% concentration and treated with a stoichiometric amount of boron trifluoride. This treatment produces a 1:1 boron trifluoride — xanthate ester complex, with the boron trifluoride complexed on the nitrile portion of the ester. The complex is then treated with an excess of water and hydrolyzes rapidly to produce an unsaturated derivative. The hydrolysis takes place in about 20 minutes to give a 50–60% yield of the unsaturated derivative.

The derivative which is produced by decomposition of the polyvinyl alcohol xanthate ester is a vinyl alcohol-acetylene copolymer which is the theoretical derivative of the partial dehydration of polyvinyl alcohol. When the product copolymer is re-xanthated and the cyanomethyl ester formed, complexed with boron trifluoride, and again hydrolyzed there is obtained a copolymer which approaches 1.00 D.S. with respect to the acetylene content of the polymer.

The vinyl alcohol — acetylene copolymer can similarly be produced by decomposition of the boron trifluoride — xanthate ester complex with other active hydrogen containing solvents as in the previous examples.

EXAMPLE 13

Sodium cellulose xanthate is reacted in aqueous suspension (or solution) with chloracetonitrile to yield the cyanomethyl ester. The xanthate ester is then slurried in diethyl ether at a concentration of about 5% and treated with a stoichiometric amount of zinc chloride. The zinc chloride — xanthate ester complex is produced in high yield. Next, the zinc chloride -xanthate ester complex is treated with an excess of water to hydrolyze the complex. The reaction goes to completion in about 1 hour and gives a yield of about 40 –50% of unsaturated cellulose, having saturation present both as vinyl unsaturation, i.e. in the 6 position, and as ring unsaturation.

When the same procedure is repeated except that the zinc chloride — xanthate ester complex is decomposed by treatment with other active hydrogen containing solvents (as described in the previous examples) there is obtained a good yield of unsaturated cellulose in a relatively short time.

EXAMPLe 14

Sodium starch xanthate is reacted in aqueous suspension (or solution) with chloracetonitrile to yield the cyanomethyl ester. The xanthate ester is then slurried in pentane at a concentration of about 5% and treated with a stoichiometric amount of ferric chloride. The ferric chloride — xanthate ester complex is produced in high yield.

Next, the ferric chloride — xanthate ester complex is treated with an excess of water to hydrolyze the complex. The reaction goes to completion in about 1 hour and gives a yield of about 40 — 50 % of unsaturated starch, having unsaturation present both as vinyl unsaturation, i.e. in the 6 position, and as ring unsaturation.

When the same procedure is repeated except that the ferric chloride — xanthate ester complex is decomposed by treatment with other active hydrogen containing solvents (as described in the previous examples) there is obtained a good yield of unsaturated starch in a relatively short time.

EXAMPLE 15

Sodium polyvinyl alcohol xanthate is reacted with chloracetonitrile in aqueous solution to yield the cyanomethyl ester.

This cyanomethyl polyvinyl alcohol xanthate ester is then slurried in methylethyl ketone at 10% concentration and treated with a stoichiometric amount of stannic chloride. This treatment produces a 1:1 stannic chloride — xanthate ester complex, with the stannic chloride complexed on the nitrile portion of the ester. The complex is then treated with an excess of water and hydrolyzes rapidly to produce an unsaturated derivative. The hydrolysis takes place in about 60 minutes to give a 50 – 60% yield of the unsaturated derivative.

The derivative which is produced by decomposition of the polyvinyl alcohol xanthate ester is a vinyl alcohol — acetylene copolymer which is the theoretical derivative of the partial dehydration of polyvinyl alcohol. When the product copolymer is re-xanthated and the cyanomethyl ester formed, complexed with stannic chloride, and again hydrolyzed there is obtained a copolymer which approaches 1.00 D.S. with respect to the polyacetylene content.

The vinyl alcohol — acetylene copolymer can similarly be produced by decomposition of the stannic chloride — xanthate ester complex with other active hydrogen containing solvents as in the previous examples.

From the foregoing examples, we have demonstrated that a variety of simple and complex unsaturated compounds can be prepared by hydrolysis (or decomposition with other active hydrogen containing solvents) of Lewis acid complexes of certain xanthate esters. We have shown that xanthate esters of the form:

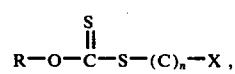

where R is an alkyl function having at least one H in a position alpha to the R—O bond, $(C)_n$ is a linear alkyl function either substituted or unsubstituted, with N = 1 - 3, X has a basicity greater than the $>C=S$ function and comprises a C or S containing functional group having at least one double or triple bond to a hetero atom, the functional group being connected to $(C)_n$ through C or S; may be reacted with Lewis acids, either neat or in non-protonic non-aqueous solvents, to yield a Lewis acid complex of the esters. The Lewis acid used must be of an acid strength such that it will form a salt or complex preferentially with the derivative functional group rather than the thione sulfur of the xanthate group. Also, when the preparation of the Lewis acid complex is carried out in solution or dispersion in a non-aqueous solution, a Lewis acid must be used which does not form a stronger complex with the solvent than with the derivative group in the xanthate ester. The Lewis acid is preferably used in an amount just sufficient to form the desired complex and not in excess so that it will react with the xanthate group. We have shown that the Lewis acid complexes are hydrolyzed rapidly at room temperature (or higher temperatures if desired) in water, or in other active hydrogen containing solvents to yield an unsaturated derivative of R.

In the xanthate esters which are used to form the Lewis acid complex to be hydrolyzed in accordance with this invention, the R group in the formula given is a simple or complex, substituted or unsubstituted, monomeric or polymeric, alkyl function having at least one H in a position alpha to the R—O bond. We have shown that the R group may be a simple alkyl group or may be a highly complex polymer and may contain substituents of any and all kinds so long as they are inert under the conditions of preparation and decomposition of the xanthate ester and do not complex preferentially with the Lewis acid used to form the intermediate complex. The X group may be any of a variety of functional groups limited only in that it has a basicity greater than the thiocarbonyl function. Typical examples of the X group include the following:

-continued

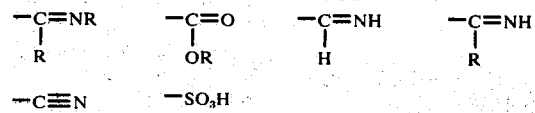

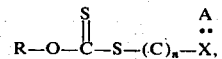

We claim:

1. A xanthate ester complex of the formula $$R-O-\overset{S}{\underset{\|}{C}}-S-(C)_n-\overset{A}{\underset{\cdot\cdot}{X}},$$

where R is an alkyl function having at least one H in a position alpha to the R—O bond, $(C)_n$ is a linear alkyl function either substituted or unsubstituted, with $n = 1 - 3$, X has a basicity greater than the $>C=S$ function and comprises a C or S containing functional group having at least one double or triple bond to a hetero atom, and functional group being connected to $(C)_n$ through C or S, and A is a Lewis acid.

2. A xanthate ester complex in accordance with claim 1 in which X is

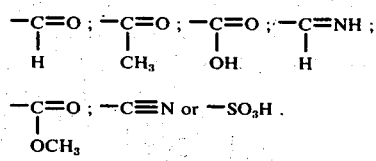

3. A method of preparing a xanthate ester complex as defined in claim 1 in which a Lewis Acid is reacted with a xanthate ester of the formula

neat or in a non-aqueous solvent.

* * * * *